US012593863B2

(12) United States Patent
Griffin et al.

(10) Patent No.: US 12,593,863 B2
(45) Date of Patent: Apr. 7, 2026

(54) PROBIOTICS TO PREVENT COGNITIVE DYSFUNCTION

(71) Applicant: DUPONT NUTRITION BIOSCIENCES APS, Kongens Lyngby (DK)

(72) Inventors: Sile Griffin, Kantvik (FI); Elaine Patterson, Kantvik (FI); Markus Lehtinen, Kantvik (FI)

(73) Assignee: INTERNATIONAL N&H DENMARK APS, Kongens Lyngby (DK)

( * ) Notice: Subject to any disclaimer, the term of this patent is extended or adjusted under 35 U.S.C. 154(b) by 428 days.

(21) Appl. No.: 18/248,077

(22) PCT Filed: Oct. 8, 2021

(86) PCT No.: PCT/EP2021/077904
§ 371 (c)(1),
(2) Date: Apr. 6, 2023

(87) PCT Pub. No.: WO2022/074216
PCT Pub. Date: Apr. 14, 2022

(65) Prior Publication Data
US 2023/0380471 A1 Nov. 30, 2023

(30) Foreign Application Priority Data
Oct. 9, 2020 (EP) .................................... 20201075

(51) Int. Cl.
| A23L 33/135 | (2016.01) |
| A61K 35/00 | (2006.01) |
| A61K 35/744 | (2015.01) |
| A61P 25/28 | (2006.01) |

(52) U.S. Cl.
CPC .......... *A23L 33/135* (2016.08); *A61K 35/744* (2013.01); *A61P 25/28* (2018.01); *A61K 2035/115* (2013.01)

(58) Field of Classification Search
CPC ... A23L 33/135; A61P 25/28; A61K 2035/115
See application file for complete search history.

(56) References Cited

U.S. PATENT DOCUMENTS

| 2023/0277608 A1* | 9/2023 | Stenman | ................... | A61P 1/00 |
| | | | | 424/93.45 |
| 2025/0032560 A1* | 1/2025 | Stenman | ................ | A61P 25/18 |

FOREIGN PATENT DOCUMENTS

WO      WO 2019/121669 A1 *  6/2019

OTHER PUBLICATIONS

Albee, Journal of Primary Prevention, 2004; 24(4): 419-436 (Year: 2004).*
Mayo Clinic, MCI-diagnosis and treatment; https://www.mayoclinic.org/diseases-conditions/mild-cognitive-impairment/diagnosis-treatment/drc-20354583?p=1; Oct. 2024 (Year: 2024).*
Mayo Clinic, MCI-summary and prevention; https://www.mayoclinic.org/diseases-conditions/mild-cognitive-impairment/symptoms-causes/syc-20354578; Oct. 2024 (Year: 2024).*
Cleveland Clinic, https://my.clevelandclinic.org/health/diseases/4865-learning-disabilities-what-you-need-to-know; Jan. 2024 (Year: 2024).*
Cleveland Clinic, https://my.clevelandclinic.org/health/diseases/24976-neurodegenerative-diseases#prevention; May 2023 (Year: 2023).*

* cited by examiner

*Primary Examiner* — Brian Gangle
*Assistant Examiner* — Lakia J Jackson-Tongue

(57) ABSTRACT

This invention relates to bacteria of the species *Lacticaseibacillus paracasei* for use in preventing or treating cognitive impairments in a subject in need thereof. This invention also relates to bacteria of the species *Lacticaseibacillus paracasei* for use in preventing or treating cognitive impairments induced by sleep deprivation and/or insufficient sleep in a subject in need thereof.

5 Claims, 4 Drawing Sheets

A

B

C

D

Abbreviations: CFU, colony forming unit; D, day; SD, sleep deprivation; Tr, training
[1] Novel Object Recognition Test; [2] Spontaneous alternation Y-maze test; [3] Step-through passive avoidance task

PROBIOTICS TO PREVENT COGNITIVE DYSFUNCTION

CROSS-REFERENCE TO RELATED PATENT APPLICATIONS

This patent claims priority under 35 USC § 371 as a national phase of Int'l Patent Appl. PCT/EP2021/077904 (filed Oct. 8, 2021; and published Apr. 14, 2022 as Int'l Publ. No. WO2022/074216), which, in turn, claims priority to European Patent Appl. 20201075.7 (filed Oct. 9, 2020). The entire text of each of the above-referenced patent applications is incorporated by reference into this patent.

FIELD OF THE INVENTION

This invention relates to bacteria of the species *Lacticaseibacillus paracasei* (previously known as *Lactobacillus paracasei*) for use in preventing or treating cognitive impairments in a subject in need thereof. This invention also relates to bacteria of the species *Lacticaseibacillus paracasei* for use in preventing or treating cognitive impairments induced by sleep deprivation and/or insufficient sleep in a subject in need thereof. This invention further relates to compositions comprising bacteria of the species *Lacticaseibacillus paracasei*, including food products, dietary supplements, and pharmaceutically acceptable formulations, methods and uses of bacteria of the species *Lacticaseibacillus paracasei* or compositions comprising bacteria of the species *Lacticaseibacillus paracasei*.

BACKGROUND

Insufficient sleep is a pervasive and prominent public health concern across the life span within the modern 24-hour (h) society and is associated with a myriad of adverse physical and mental dysfunctions. The National Sleep Foundation recommend that adults (18-64 years) require between 7-9 h of sleep per day to maintain overall health and well-being, as well as cognitive, emotional, and physical health (Hirshkowitz et al. 2015). The reality is that approximately one third of adults in most industrialized countries report reduced sleep duration (i.e. less than 7 h of sleep per day) (Owen and Veasey 2020), and continuous sleep deprivation (SD) is linked to 7 of the 15 leading causes of death in the United States of America, related to infection, cardiovascular complications and metabolic dysfunction, among others (Chattu et al. 2019). Furthermore, repeated sleep loss has severe consequences on work efficiency, public safety, overall well-being (Magnavita and Garbarino 2017; Simon and Walker 2018), and is known to influence sleep disorders including insomnia, psychiatric illnesses such as mood, depression, and anxiety, and addiction disorders (Geoffroy et al. 2020).

Numerous sleep deprivation studies have unveiled various aspects of sleep architecture (Toth and Bhargava 2013) and determined the neurobehavioural consequences of sleep loss on cognitive performance including attention and working memory, and other functions such as long-term memory and decision-making (Krause et al. 2017). Cognitive enhancing interventions, such as caffeine and modafinil have been reported to reverse sleep deprivation-induced cognitive impairment in humans and in animal models (Colavito et al. 2013), however such interventions are associated with numerous side effects such as disorientation, habituation, and daytime fatigue. Thus, there is an unmet need to investigate pharmacological interventions and dietary supplements with less side effects and high efficacy to counteract the cognitive deficits caused by sleep deprivation.

The microbiota-gut-brain axis, a bidirectional dialogue between the gut microbiota and the central nervous system, presents an attractive target for the development of novel therapeutics related to enhancing cognitive function and/or alleviating cognitive dysfunction. In this context, different *Lactobacillus* strains, either alone or in combinations, have been shown to improve cognitive functions in various rodent models, for example (Stenman et al. 2020; Liang et al. 2015). In another study, intervention with specific *Bifidobacterium* strains in healthy mice selectively improved object recognition memory, decreased the number of errors in a spatial memory test, and induced better long-term learning in fear conditioning (Savignac et al. 2014). The safety and efficacy of *Bifidobacterium breve* A1 in preventing cognitive impairment has been reported in a mouse model of Alzheimer's disease and participants with mild cognitive impairment (Kobayashi et al. 2019; Kobayashi et al. 2017). Deficits in cognitive function following sleep deprivation have also previously been reported in mice and the probiotic bacterial strain, *Lactobacillus plantarum* MTCC 9510 has proven efficacious in alleviating such cognitive disruption (Dhaliwal et al. 2018). Interestingly, in healthy older adults, better sleep quality has been shown to be associated with improved performance on cognitive tasks and higher proportions of certain gut microbial phyla, suggesting a possible relationship between sleep quality, the gut microbiome, and cognitive flexibility (Anderson et al. 2017).

OBJECT OF INVENTION

Considering the important linkages between the microbiota-gut-brain axis, sleep physiology and cognition, modulating the gut microbiota composition or influencing the mucosal physiology directly with probiotic supplementation has the potential to ameliorate sleep deprivation-induced deficits to cognitive function. To examine this hypothesis, a paradigm of repetitive partial sleep deprivation amongst three behavioural tests of cognition was established in mice to investigate whether the probiotic strains (*Lactiplantibacillus plantarum* Lp-115 (previously known as *Lactobacillus plantarum*) (Lp-115), *Lacticaseibacillus paracasei* Lpc-37 (previously known as *Lactobacillus paracasei*) (Lpc-37), *Bifidobacterium animalis* ssp. *lactis* 420 (13420)) and their combination could prevent or treat cognitive impairments due, for example, to sleep deprivation and/or insufficient sleep.

SUMMARY OF THE INVENTION

The present invention is based on studies described herein which surprisingly demonstrate that strains of the species *Lacticaseibacillus paracasei, Lactiplantibacillus plantarum, Bifidobacterium animalis* ssp. *lactis* and their combination can prevent or treat cognitive impairments induced, for example, by sleep deprivation and/or insufficient sleep.

Accordingly, in one aspect, the invention provides a bacterial strain of the species *Lacticaseibacillus paracasei* or a mixture thereof for use in preventing or treating cognitive impairments in a subject in need thereof.

In yet a further aspect, the invention provides a composition comprising a bacterial strain of the species *Lacticaseibacillus paracasei* or a mixture thereof for use in preventing or treating cognitive impairments in a subject in need thereof.

In a further aspect, the invention provides a method of preventing or treating cognitive impairments in a subject in need thereof, said method comprising administering a bacterial strain or a composition comprising a bacterial strain to said subject, wherein said bacterial strain is of the species *Lacticaseibacillus paracasei* or a mixture thereof.

DETAILED DESCRIPTION OF INVENTION

Figure 1:
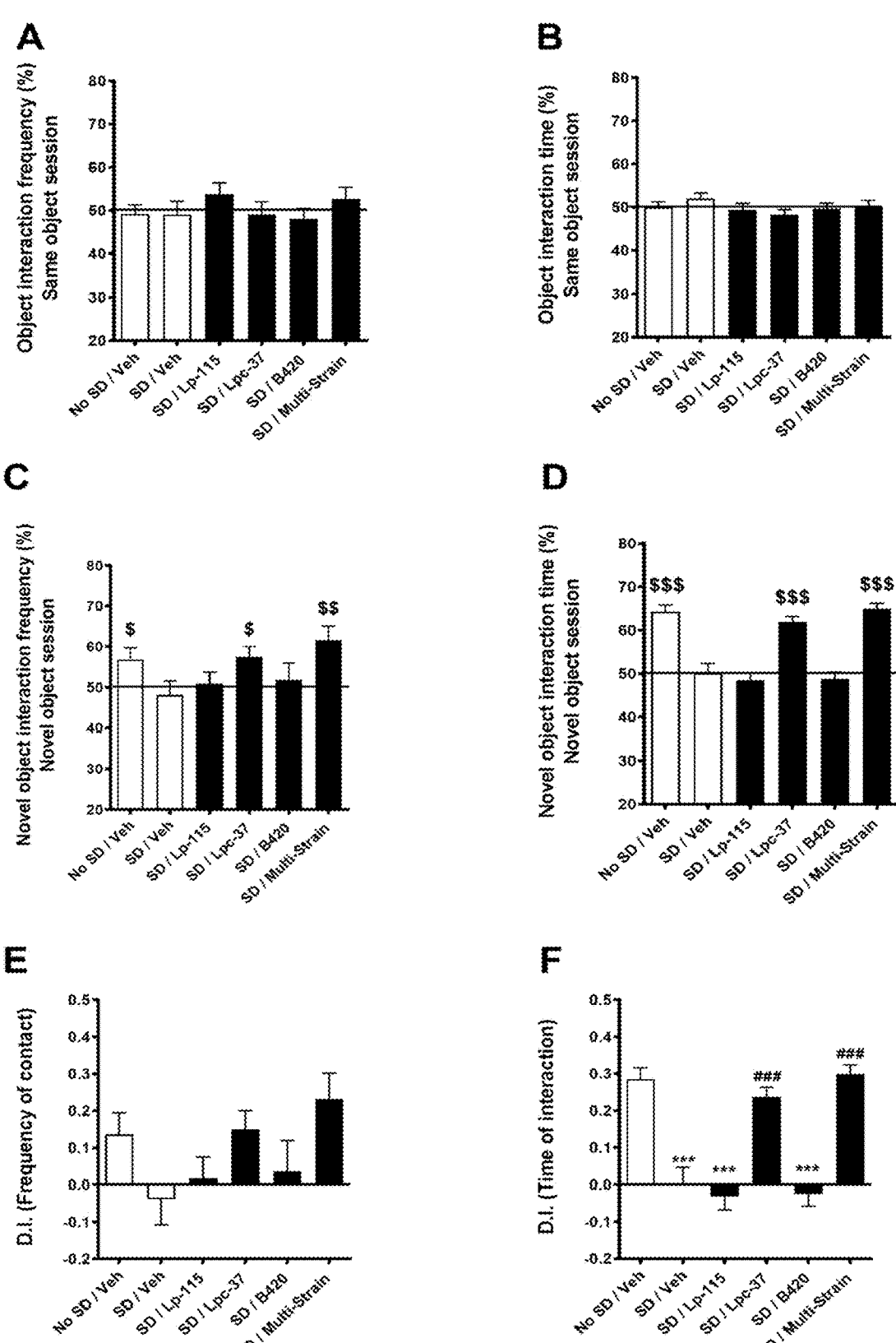
FIG. 1. Novel object recognition test (recognition memory). Effects of probiotic intervention on recognition memory deficits induced by sleep deprivation (SD). Cognitive function in the novel object recognition test following administration of either $1 \times 10^9$ colony forming units of bacterial strain (Lp-115 or Lpc-37 or B420), $1.5 \times 10^9$ colony forming units of bacterial combination (Lp-115+Lpc-37+B420) or vehicle for 30 days prior to and for 9 days during a behavioural test paradigm. (A and B) Object interaction frequency (%) and object interaction time (%) during the same object session on training day (Day 2), respectively. (C and D) Object interaction frequency (%) and object interaction time (%) during the novel object session on test day (Day 3), respectively. (E and F) Discrimination index (interaction frequency) and discrimination index (interaction time), during the novel object session on test day (Day 3), respectively.

The detailed aspects of this invention are set out below. In part some of the detailed aspects are discussed in separate sections. This is for ease of reference and is in no way limiting. All of the embodiments described below are equally applicable to all aspects of the present invention unless the context specifically dictates otherwise.

Bacteria

The bacteria used in aspects of the invention are bacteria of the species *Lacticaseibacillus paracasei*. In one aspect, the *Lacticaseibacillus paracasei* is strain Lpc-37, also known as Lbc81. This strain is commercially available from DuPont Nutrition Biosciences ApS. This strain of *Lacticaseibacillus paracasei* was also deposited under the reference DGCC4981 by DuPont Nutrition Biosciences ApS, of Langebrogade 1, DK-1411 Copenhagen K, Denmark, in accordance with the Budapest Treaty on 5 Oct. 2017 at the Leibniz-Institut Deutsche Sammlung von Mikroorganismen and Zellkulturen GmbH (DSMZ), Inhoffenstrasse 7B, 38124 Braunschweig, Germany, where it is recorded under registration number DSM 32661.

Other bacteria used in aspects of the invention are bacteria of the species *Bifidobacterium animalis* ssp. *lactis*. In a particularly preferred embodiment, the bacteria used in the present invention are *Bifidobacterium animalis* ssp. *lactis* strain 420 (B420). This strain is commercially available from DuPont Nutrition Biosciences ApS. This strain of *Bifidobacterium animalis* ssp. *lactis* was also deposited under the reference DGCC420 by DuPont Nutrition Biosciences ApS, of Langebrogade 1, DK-1411 Copenhagen K, Denmark, in accordance with the Budapest Treaty on 30 Jun. 2015 at the Leibniz-Institut Deutsche Sammlung von Mikroorganismen and Zellkulturen GmbH (DSMZ), Inhoffenstrasse 7B, 38124 Braunschweig, Germany, where it is recorded under registration number DSM 32073.

Other bacteria used in aspects of the invention are bacteria of the species *Lactiplantibacillus plantarum*. In one aspect, the *Lactiplantibacillus plantarum* is strain Lp-115. This strain is commercially available from DuPont Nutrition Biosciences ApS.

Preferably the bacterial strains used in the present invention are bacterial strains which are generally recognised as safe (GRAS) and, which are preferably GRAS approved. GRAS is an American Food and Drug Administration (FDA) designation that a chemical or substance added to food is considered safe by experts, and so is exempted from the usual Federal Food, Drug, and Cosmetic Act (FFDCA) food additive tolerance requirements.

In a first aspect, the present invention provides bacterial strain of the species *Lacticaseibacillus paracasei* or a mixture thereof for use in preventing or treating cognitive impairments in a subject in need thereof.

Cognitive impairment is often defined as the situation when a person has trouble remembering, learning new things, concentrating, or making decisions that affect their everyday life. Cognitive impairment can range from mild to severe. With mild impairment, people may begin to notice changes in cognitive functions, but still be able to do their everyday activities. Severe levels of impairment can lead to losing the ability to understand the meaning or importance of something and the ability to talk or write, resulting in the inability to live independently. The cognitive impairments are often due to mental fatigue. Mental fatigue includes symptoms of attention deficiencies, lack of focusing, forgetfulness, lack of productivity, lack of concentration, reduced mental clarity, problem paying attention, short attention span and learning difficulties.

In another aspect, the present invention provides bacterial strain for use in preventing or treating cognitive impairments wherein the cognitive impairments are induced by sleep deprivation and/or insufficient sleep. The sleep deprivation and/or insufficient sleep can be due to a sleep disorder. The sleep disorder is or can be sleep apnea, narcolepsy, insomnia and/or parasomnia.

In one aspect, the cognitive impairments are learning and memory deficits.

In another aspect, the cognitive impairments are recognition memory, spatial working memory, and/or contextual long-term memory deficits.

Cognitive impairments contribute to neuropsychiatric conditions, mental illness and/or neurodegenerative diseases. The neuropsychiatric conditions and/or mental illness are mood disorders, depression, anxiety, neurotic disorders and addiction disorders. Neurodegenerative diseases are dementia, Parkinson's disease, Alzheimer's disease, vascular dementia, dementia with Lewy bodies, Huntington's disease, progressive supranuclear palsy, frontotemporal dementia, Creutzfeldt-Jakob disease, Wernicke-Korsakoff syndrome.

According to the present invention, the *Lacticaseibacillus paracasei* may be used in combination with one or more other bacterial species which have the ability to exert positive health benefits on the host to which they are administered.

The *Lacticaseibacillus paracasei* may be used in any form (for example viable, dormant, inactivated or dead bacteria) provided that the bacterium remains capable of exerting the effects described herein. Preferably, the *Lacticaseibacillus paracasei* used in aspects of the invention is viable.

Preferably, the *Lacticaseibacillus paracasei* and, when used in aspects of the invention, other bacterial species, is suitable for human and/or animal consumption. A skilled person will be readily aware of specific strains of *Lacticaseibacillus paracasei* and other bacterial strains which are used in the food and/or agricultural industries and which are generally considered suitable for human and/or animal consumption.

Optionally, the *Lacticaseibacillus paracasei* and, when used in aspects of the invention, other bacterial strains, are probiotic bacteria. The term "probiotic bacteria" is defined as covering any non-pathogenic bacteria which, when administered live in adequate amounts to a host, confers a health benefit on that host. For classification as a "probiotic", the bacteria must survive passage through the upper part of the digestive tract of the host. They are non-pathogenic, non-toxic and exercise their beneficial effect on health on the one hand via ecological interactions with the resident flora in the digestive tract, and on the other hand via their ability to influence the host physiology and immune system in a positive manner. Probiotic bacteria, when administered to a host in sufficient numbers, have the ability to progress through the intestine, maintaining viability, exerting their primary effects in the lumen and/or the wall of the host's gastrointestinal tract. They then transiently form part of the resident flora and this colonisation (or transient colonisation) allows the probiotic bacteria to exercise a beneficial effect, such as the repression of potentially pathogenic micro-organisms present in the flora and interactions with the host in the intestine including the immune system.

Thus, in a particular aspect of the present invention, the bacterial strain for use according to the invention is a probiotic strain. In particular, the strain of the species *Lacticaseibacillus paracasei* is strain Lpc-37, registered at the DSMZ under deposit number DSM32661 on 5 Oct. 2017.

Compositions

The term "composition" is used in the broad sense to mean the way something is composed, i.e. its general makeup. In aspects of the invention, the compositions may consist essentially of a single strain of the species *Lacticaseibacillus paracasei* bacteria.

Alternatively, the compositions may comprise a *Lacticaseibacillus paracasei* strain together with other components, such as other bacterial strains, biological and chemical components, active ingredients, metabolites, nutrients, fibres, prebiotics, etc. In a particular aspect of the present invention, the other bacterial strains present in the compositions are strains Lp-115 and/or strain B420 (strain B420 is registered at the DSMZ under deposit number DSM32073 dated 30 Jun. 2015).

In one aspect, the present invention provides a composition comprising a bacterial strain of the species *Lacticaseibacillus paracasei* or a mixture thereof for use in preventing or treating cognitive impairments in a subject in need thereof.

According to the present invention, the cognitive impairments are, or can be, induced by sleep deprivation and/or insufficient sleep. In a particular aspect of the present invention, the cognitive impairments are learning and memory deficits. In another particular aspect of the present invention, the cognitive impairments are recognition memory, spatial working memory, and/or contextual long-term memory deficits.

In a particular aspect, the sleep deprivation and/or insufficient sleep can be due to a sleep disorder. In another aspect of the invention, the sleep disorder is or can be sleep apnea, narcolepsy, insomnia and/or parasomnia.

In another aspect of the present invention, the cognitive impairments contribute to neuropsychiatric conditions, mental illness and/or neurodegenerative diseases. The neuropsychiatric conditions and/or mental illness are, or can be, mood disorders, depression, anxiety, neurotic disorders and addiction disorders.

In a further and particular aspect of the present invention, the neurodegenerative diseases are dementia, Parkinson's disease, Alzheimer's disease, vascular dementia, dementia with Lewy bodies, Huntington's disease, progressive supranuclear palsy, frontotemporal dementia, Creutzfeldt-Jakob disease, Wernicke-Korsakoff syndrome.

In a yet further aspect of the present invention, the cognitive impairments are due to mental fatigue. In a particular aspect, mental fatigue includes symptoms of attention deficiencies, lack of focusing, forgetfulness, lack of productivity, lack of concentration, reduced mental clarity, problem paying attention, short attention span and learning difficulties.

In particular, the bacterial strains of the compositions according to the present invention are probiotic strains.

In another particular case according to the present invention, the strain of the compositions is strain Lpc-37, registered at the DSMZ under deposit number DSM32661 on 5 Oct. 2017.

According to one aspect of the present invention, the composition is a spray-dried or freeze-dried composition.

According to another aspect of the present invention, the composition comprises a cryoprotectant.

In yet a further aspect of the present invention, the bacterial strain of the species *Lacticaseibacillus paracasei* is present in the composition in an amount between $10^6$ and $10^{12}$, e.g. between $10^8$ and $10^{12}$ colony forming units (CFU) per dose, optionally $10^{10}$ CFU per dose.

While it is not a requirement that the compositions comprise any support, diluent or excipient, such a support, diluent or excipient may be added and used in a manner which is familiar to those skilled in the art. Examples of suitable excipients include, but are not limited to, microcrystalline cellulose, rice maltodextrin, silicone dioxide, and magnesium stearate. The compositions of the invention may also comprise cryoprotectant components (for example, glucose, sucrose, lactose, trehalose, sodium ascorbate and/or other suitable cryoprotectants).

The terms "composition" and "formulation" may be used interchangeably.

Compositions used in aspects of the invention may take the form of solid, liquid, solution or suspension preparations. Examples of solid preparations include, but are not limited to: tablets, pills, capsules, granules and powders which may be wettable, spray-dried or freeze dried/lyophilized. The compositions may contain flavouring or colouring agents. The compositions may be formulated for immediate-, delayed-, modified-, sustained-, pulsed- or controlled-release applications.

By way of example, if the compositions of the present invention are used in a tablet form, the tablets may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of other acceptable carriers for use in preparing compositions include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, hydroxymethylcellulose, polyvinylpyrrolidone, and the like.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

Specific non-limiting examples of compositions which can be used in aspects of the invention are set out below for illustrative purposes. These include, but are not limited to food products, food ingredients, functional foods, dietary supplements, pharmaceutical compositions and medicaments.

Food Products

The compositions of the invention may take the form of a food product. Here, the term "food" is used in a broad sense and covers food and drink for humans as well as food and drink for animals (i.e. a feed). Preferably, the food product is suitable for, and designed for, human consumption.

The food may be in the form of a liquid, solid or suspension, depending on the use and/or the mode of application and/or the mode of administration.

When in the form of a food product, the composition may comprise or be used in conjunction with one or more of: a nutritionally acceptable carrier, a nutritionally acceptable diluent, a nutritionally acceptable excipient, a nutritionally acceptable adjuvant, a nutritionally active ingredient.

By way of example, the compositions of the invention may take the form of one of the following:

A fruit juice; a beverage comprising whey protein: a health or herbal tea, a cocoa drink, a milk drink, a lactic acid bacteria drink, a yoghurt and/or a drinking yoghurt, a cheese, an ice cream, a water ice, a dessert, a confectionery, a biscuit, a cake, cake mix or cake filling, a snack food, a fruit filling, a cake or doughnut icing, an instant bakery filling cream, a filling for cookies, a ready-to-use bakery filling, a reduced calorie filling, an adult nutritional beverage, an acidified soy/juice beverage, a nutritional or health bar, a beverage powder, a calcium fortified soy milk, or a calcium fortified coffee beverage.

Optionally, where the product is a food product, the bacterium *Lacticaseibacillus paracasei* should remain effective through the normal "sell-by" or "expiration" date during which the food product is offered for sale by the retailer. Preferably, the effective time should extend past such dates until the end of the normal freshness period when food spoilage becomes apparent. The desired lengths of time and normal shelf life will vary from foodstuff to foodstuff and those of ordinary skill in the art will recognise that shelf-life times will vary upon the type of foodstuff, the size of the foodstuff, storage temperatures, processing conditions, packaging material and packaging equipment.

Food Ingredients

Compositions of the present invention may take the form of a food ingredient and/or feed ingredient.

As used herein the term "food ingredient" or "feed ingredient" includes a composition which is or can be added to functional foods or foodstuffs as a nutritional and/or health supplement for humans and animals.

The food ingredient may be in the form of a liquid, suspension or solid, depending on the use and/or the mode of application and/or the mode of administration.

Functional Foods

Compositions of the invention may take the form of functional foods.

As used herein, the term "functional food" means food which is capable of providing not only a nutritional effect but is also capable of delivering a further beneficial effect to the consumer.

Accordingly, functional foods are ordinary foods that have components or ingredients (such as those described herein) incorporated into them that impart to the food a specific function—e.g. medical or physiological benefit—other than a purely nutritional effect.

Although there is no legal definition of a functional food, most of the parties with an interest in this area agree that they are foods marketed as having specific health effects beyond basic nutritional effects.

Some functional foods are nutraceuticals. Here, the term "nutraceutical" means a food which is capable of providing not only a nutritional effect and/or a taste satisfaction but is also capable of delivering a therapeutic (or other beneficial) effect to the consumer. Nutraceuticals cross the traditional dividing lines between foods and medicine.

Dietary Supplements

The compositions of the invention may take the form of dietary supplements or may themselves be used in combination with dietary supplements, also referred to herein as food supplements.

The term "dietary supplement" as used herein refers to a product intended for ingestion that contains a "dietary ingredient" intended to add nutritional value or health benefits to (supplement) the diet. A "dietary ingredient" may include (but is not limited to) one, or any combination, of the following substances: bacteria, a probiotic (e.g. probiotic bacteria), a vitamin, a mineral, a herb or other botanical, an amino acid, a dietary substance for use by people to supplement the diet by increasing the total dietary intake, a concentrate, metabolite, constituent, or extract.

Dietary supplements may be found in many forms such as tablets, capsules, soft gels, gel caps, liquids, or powders. Some dietary supplements can help ensure an adequate dietary intake of essential nutrients; others may help reduce risk of disease.

Pharmaceutical Compositions

Compositions of the invention may be used as—or in the preparation of—pharmaceuticals. Here, the term "pharmaceutical" is used in a broad sense—and covers pharmaceuticals for humans as well as pharmaceuticals for animals (i.e. veterinary applications). In a preferred aspect, the pharmaceutical is for human use.

The pharmaceutical can be for therapeutic purposes—which may be curative, palliative or preventative in nature.

A pharmaceutical may be in the form of a compressed tablet, tablet, capsule, ointment, suppository or drinkable solution.

When used as—or in the preparation of—a pharmaceutical, the compositions of the present invention may be used in conjunction with one or more of: a pharmaceutically acceptable carrier, a pharmaceutically acceptable diluent, a pharmaceutically acceptable excipient, a pharmaceutically acceptable adjuvant, a pharmaceutically active ingredient.

The pharmaceutical may be in the form of a liquid or as a solid—depending on the use and/or the mode of application and/or the mode of administration.

The *Lacticaseibacillus paracasei* used in the present invention may itself constitute a pharmaceutically active ingredient. In one embodiment, the *Lacticaseibacillus paracasei* constitutes the sole active component. Alternatively, the *Lacticaseibacillus paracasei* may be at least one of a number (i.e. two or more) of pharmaceutically active components.

Medicaments

Compositions of the invention may take the form of medicaments.

The term "medicament" as used herein encompasses medicaments for both human and animal usage in human and veterinary medicine. In addition, the term "medicament" as used herein means any substance which provides a therapeutic, preventative and/or beneficial effect. The term "medicament" as used herein is not necessarily limited to substances which need marketing approval but may include substances which can be used in cosmetics, nutraceuticals, food (including feeds and beverages for example), probiotic cultures, and natural remedies. In addition, the term "medicament" as used herein encompasses a product designed for incorporation in animal feed, for example livestock feed and/or pet food.

Medical Foods

Compositions of the present invention may take the form of medical foods.

By "medical food" it is meant a food which is formulated to be consumed or administered with or without the supervision of a physician and which is intended for a specific dietary management or condition for which distinctive nutritional requirements, based on recognized scientific principles, are established by medical evaluation.

Dosage

The compositions of the present invention may comprise from $10^6$ to $10^{12}$ colony forming units (CFU) of bacterial strain(s) per dose or per gram of composition, and more particularly from $10^8$ to $10^{12}$ CFU of bacterial strain(s) per dose or per gram of composition. Optionally the compositions comprise about $10^{10}$ CFU of bacterial strain(s) per dose or per gram of composition.

The bacterial strains(s), for example *Lacticaseibacillus paracasei* (such as strain Lpc-37), and/or strain Lp-115 and/or strain B420, may be administered at a dosage from about $10^6$ to about $10^{12}$ CFU of bacterial strain per dose, preferably about $10^8$ to about $10^{12}$ CFU of bacterial strain per dose. By the term "per dose" it is meant that this number of bacteria is provided to a subject either per day or per intake, preferably per day. For example, if the bacteria are to be administered in a food product, for example in a yoghurt, then the yoghurt may contain from about $10^6$ to $10^{12}$ CFU of the bacterial strain. Alternatively, however, this number of bacteria may be split into multiple administrations, each consisting of a smaller amount of microbial loading—so long as the overall amount of bacterial strain received by the subject in any specific time, for instance each 24 h period, is from about $10^6$ to about $10^{12}$ CFU of bacteria, optionally $10^8$ to about $10^{12}$ CFU of bacteria.

In accordance with the present invention an effective amount of at least one bacterial strain may be at least $10^6$ CFU of bacteria/dose, optionally from about $10^8$ to about $10^{12}$ CFU of bacteria/dose, e.g., about $10^{10}$ CFU of bacteria/dose.

In one embodiment, the *Lacticaseibacillus paracasei* (e.g. strain Lpc-37/DSM 32661), may be administered at a dosage from about $10^6$ to about $10^{12}$ CFU of bacteria/day, optionally about $10^8$ to about $10^{12}$ CFU of bacteria/day. Hence, the effective amount in this embodiment may be from about $10^6$ to about $10^{12}$ CFU of bacteria/day, optionally about $10^8$ to about $10^{12}$ CFU of bacteria/day.

In a particular embodiment, an amount of $1 \times 10^9$ CFU of single bacterial strain or $1.5 \times 10^9$ CFU of bacterial multi-strain (for example Lpc-37 at $5 \times 10^8$ CFU, Lp-115 at $5 \times 10^8$ CFU and B420 at 8 CFU) were administered.

Effects/Subjects/Medical Indications

In one embodiment, the term "subject", as used herein, means a mammal, including for example livestock (for example cattle, horses, pigs, and sheep) and humans. In one embodiment the subject is a human. In one embodiment the subject is female. In one embodiment the subject is male. In another embodiment, the subject is a dog (such as a member of the genus *Canis*) or a cat (such as a member of the genera *Felis* or *Panthera*). In another embodiment, the subject is poultry, for example chicken, turkeys, ducks and geese. In preferred embodiments, the bacterial strain and compositions are for use in a human.

The bacterial strains and/or compositions of the present invention can be used for preventing or treating cognitive impairments in a subject in need thereof.

According to the Centers for Disease Control and Prevention (CDC), "cognitive impairment" is when a person has trouble remembering, learning new things, concentrating, or making decisions that affect their everyday life. Cognitive impairment ranges from mild to severe. With mild impairment, people may begin to notice changes in cognitive functions, but still be able to do their everyday activities. Severe levels of impairment can lead to losing the ability to understand the meaning or importance of something and the ability to talk or write, resulting in the inability to live independently.

Cognitive impairments can be, for example, the result of sleep deprivation and/or insufficient sleep. Sleep deprivation and/or insufficient sleep can be a consequence of a sleep disorder, such as apnea, narcolepsy, insomnia and/or parasomnia.

Disorders associated with cognitive impairment are, for example, learning and memory deficits, recognition memory, spatial working memory, contextual long-term memory deficits, mood disorders, depression, anxiety, neurotic disorders, addiction disorders, dementia, Parkinson's disease, Alzheimer's disease, vascular dementia, dementia with Lewy bodies, Huntington's disease, progressive supranuclear palsy, frontotemporal dementia, Creutzfeldt-Jakob disease, Wernicke-Korsakoff syndrome, attention deficiencies, lack of focusing, forgetfulness, lack of productivity, lack of concentration, reduced mental clarity, problem paying attention, short attention span and learning difficulties.

Prebiotics

In one embodiment, the bacterial strains and compositions of the present invention may further be combined or comprise one or more fibres and/or prebiotics.

Prebiotics are defined as a substrate that is selectively utilized by host microorganisms conferring a health benefit. These are generally ingredients that beneficially affect the health of the host by selectively stimulating the growth and/or activity of one or a limited number of bacteria, and thus improve host health. The prebiotic can be applied to oral route, but it can be also applied to other microbially colonized sites. Typically, prebiotics are carbohydrates (such as oligosaccharides), but the definition does not preclude non-carbohydrates, such as polyphenols, or polyunsaturated fatty acids or other ingredients that can be utilized selectively by a limited number of bacteria to confer a health benefit. The most prevalent forms of prebiotics are nutritionally classed as soluble fibres. To some extent, many forms of dietary fibres exhibit some level of prebiotic effect.

In one embodiment, a prebiotic is a selectively fermented ingredient that allows specific changes, both in the composition and/or activity in the gastrointestinal or skin microflora that confers benefits upon host well-being and health.

Suitably, the prebiotic may be used according to the present invention in an amount of 0.01 to 100 g/day, preferably 0.1 to 50 g/day, more preferably 0.5 to 20 g/day. In one embodiment, the prebiotic may be used according to the present invention in an amount of 1 to 10 g/day, preferably 2 to 9 g/day, more preferably 3 to 8 g/day. In another embodiment, the prebiotic may be used according to the present invention in an amount of 5 to 50 g/day, preferably 5 to 25 g/day.

Examples of dietary sources of prebiotics include soybeans, inulin sources (such as Jerusalem artichoke, jicama, and chicory root), raw oats, unrefined wheat, unrefined barley and yacon.

Examples of suitable prebiotics include alginate, xanthan, pectin, locust bean gum (LBG), inulin, guar gum, galacto-oligosaccharide (GOS), fructo-oligosaccharide (FOS), poly-dextrose 10 (i.e. Litesse®), lactitol, L-Arabinose, D-Xylose, L-Rhamnose, D-Mannose, L-Fucose, inositol, sorbitol, mannitol, xylitol, fructose, carrageenan, alginate, microcrystalline cellulose (MCC), betaine, lactosucrose, soybean oligosaccharides, isomaltulose (Palatinose™), isomalto-oligosaccharides, gluco-oligosaccharides, xylooligosaccharides, manno-oligosaccharides, beta-glucans, cellobiose, raffinose, gentiobiose, melibiose, xylobiose, cyciodextrins, isomaltose, trehalose, stachyose, panose, pullulan, verbascose, galactomannans, (human) milk oligosaccharides and all forms of resistant starches.

The combination of one or more of the bacterial strains according to the present invention and one or more fibres and/or prebiotics according to the present invention exhibits a synergistic effect in certain applications (i.e. an effect which is greater than the additive effect of the bacteria when used separately).

In one embodiment, the bacterial strains or a mixture thereof according to the present invention is used in combination with one or more fibres and/or prebiotic.

Suitably, the prebiotic used is polydextrose, lactitol, inositol, L-Arabinose, D-Xylose, L-Rhamnose, D-Mannose, L-Fucose, sorbitol, mannitol, xylitol, fructose, carrageenan, alginate, 5 microcrystalline cellulose (MCC), milk oligosaccharide or betaine.

In a further aspect, the invention relates to a composition, food products, food ingredient, dietary supplements or a pharmaceutical acceptable composition comprising bacterial strains according to the present invention or a mixture thereof and one or more fibres and/or a prebiotic.

METHODS, USES AND OTHER EMBODIMENTS OF THE INVENTION

In one aspect, the present invention provides a method of preventing or treating cognitive impairments in a subject in need thereof, said method comprising administering a bacterial strain or a composition comprising a bacterial strain to said subject, wherein said bacterial strain is of the species *Lacticaseibacillus paracasei* or a mixture thereof.

For the avoidance of doubt, the bacterial strains and any of the compositions described in the present invention can be utilised in the methods and use aspects of the invention. For example, further embodiments include, but are not limited to, those set out below:

Embodiment 1. Bacterial strain of the species *Lacticaseibacillus paracasei* or a mixture thereof for use in preventing or treating cognitive impairments in a subject in need thereof.

Embodiment 2. Bacterial strain for use according to embodiment 1, wherein the cognitive impairments are induced by sleep deprivation and/or insufficient sleep.

Embodiment 3. The bacterial strain for use according to embodiment 1, wherein the cognitive impairments are learning and memory deficits.

Embodiment 4. The bacterial strain for use according to embodiment 1, wherein the cognitive impairments are recognition memory, spatial working memory, and/or contextual long-term memory deficits.

Embodiment 5. The bacterial strain for use according to embodiment 1, wherein the cognitive impairments contribute to neuropsychiatric conditions, mental illness and/or neurodegenerative diseases.

Embodiment 6. The bacterial strain for use according to embodiment 5, wherein the neuropsychiatric conditions and/or mental illness are mood disorders, depression, anxiety, neurotic disorders and addiction disorders.

Embodiment 7. The bacterial strain for use according to embodiment 5, wherein the neurodegenerative diseases are dementia, Parkinson's disease, Alzheimer's disease, vascular dementia, dementia with Lewy bodies, Huntington's disease, progressive supranuclear palsy, frontotemporal dementia, Creutzfeldt-Jakob disease, Wernicke-Korsakoff syndrome.

Embodiment 8. The bacterial strain for use according to embodiment 2, wherein the sleep deprivation and/or insufficient sleep are due to a sleep disorder.

Embodiment 9. The bacterial strain for use according to embodiment 8, wherein the sleep disorder is sleep apnea, narcolepsy, insomnia and/or parasomnia.

Embodiment 10. The bacteria strain for use according to any one of embodiments 1-9, wherein the cognitive impairments are due to mental fatigue.

Embodiment 11. The bacterial strain according to embodiment 10, wherein mental fatigue includes symptoms of attention deficiencies, lack of focusing, forgetfulness, lack of productivity, lack of concentration, reduced mental clarity, problem paying attention, short attention span and learning difficulties.

Embodiment 12. The bacterial strain for use according to any one of the preceding embodiments, wherein the bacterial strain of the species *Lacticaseibacillus paracasei* or a mixture thereof is a probiotic strain.

Embodiment 13. The bacterial strain for use according to any one of the embodiments 1-12, wherein the strain of the species *Lacticaseibacillus paracasei* is strain Lpc-37, registered at the DSMZ under deposit number DSM32661 on 5 Oct. 2017.

Embodiment 14. Composition comprising a bacterial strain of the species *Lacticaseibacillus paracasei* or a mixture thereof for use in preventing or treating cognitive impairments in a subject in need thereof.

Embodiment 15. The composition for use according to embodiment 14, wherein the cognitive impairments are induced by sleep deprivation and/or insufficient sleep.

Embodiment 16. The composition for use according to embodiment 14, wherein the cognitive impairments are learning and memory deficits.

Embodiment 17. The composition for use according to embodiment 14, wherein the cognitive impairments are recognition memory, spatial working memory, and/or contextual long-term memory deficits.

Embodiment 18. The composition for use according to embodiment 14, wherein the cognitive impairments contribute to neuropsychiatric conditions, mental illness and/or neurodegenerative diseases.

Embodiment 19. The composition for use according to embodiment 18, wherein the neuropsychiatric conditions and/or mental illness are mood disorders, depression, anxiety, neurotic disorders and addiction disorders.

Embodiment 20. The composition for use according to embodiment 19, wherein the neurodegenerative diseases are dementia, Parkinson's disease, Alzheimer's disease, vascular dementia, dementia with Lewy bodies, Huntington's disease, progressive supranuclear palsy, frontotemporal dementia, Creutzfeldt-Jakob disease, Wernicke-Korsakoff syndrome.

Embodiment 21. The composition for use according to embodiment 15, wherein the sleep deprivation and/or insufficient sleep are due to a sleep disorder.

Embodiment 22. The composition for use according to embodiment 21, wherein the sleep disorder is sleep apnea, narcolepsy, insomnia and/or parasomnia.

Embodiment 23. The composition for use according to embodiments 14-22, wherein the cognitive impairments are due to mental fatigue.

Embodiment 24. The composition for use according to embodiment 23, wherein mental fatigue includes symptoms of attention deficiencies, lack of focusing, forgetfulness, lack of productivity, lack of concentration, reduced mental clarity, problem paying attention, short attention span and learning difficulties.

Embodiment 25. The composition for use according to any one of embodiments 14-24, wherein the bacterial strain of the species *Lacticaseibacillus paracasei* or a mixture thereof is a probiotic strain.

Embodiment 26. The composition for use according to any one of embodiments 14-25, wherein the strain of the species *Lacticaseibacillus paracasei* is strain Lpc-37, registered at the DSMZ under deposit number DSM32661 on 5 Oct. 2017.

Embodiment 27. The composition for use according to any one of embodiments 14-26, wherein said composition comprises further bacteria.

Embodiment 28. The composition for use according to embodiment 27, wherein said further bacteria is strain Lp-115 and/or strain B420, registered at the DSMZ under deposit number DSM32073 on 30 Jun. 2015.

Embodiment 29. The composition according to any one of embodiments 14-28, wherein said composition is a food product, food ingredient, a dietary supplement or a pharmaceutical composition.

Embodiment 30. Method of preventing or treating cognitive impairments in a subject in need thereof, said method comprising administering a bacterial strain or a composition comprising a bacterial strain to said subject, wherein said bacterial strain is of the species *Lacticaseibacillus paracasei* or a mixture thereof.

Embodiment 31. The method according to embodiment 30, wherein the cognitive impairments are induced by sleep deprivation and/or insufficient sleep.

Embodiment 32. The method according to embodiment 30, wherein the cognitive impairments are learning and memory deficits.

Embodiment 33. The method according to embodiment 30, wherein the cognitive impairments are recognition memory, spatial working memory, and/or contextual long-term memory deficits.

Embodiment 34. The method according to embodiment 30, wherein the cognitive impairments contribute to neuropsychiatric conditions, mental illness and/or neurodegenerative diseases.

Embodiment 35. The method according to embodiment 34, wherein the neuropsychiatric conditions and/or mental illness are mood disorders, depression, anxiety, neurotic disorders and addiction disorders.

Embodiment 36. The method according to embodiment 35, wherein the neurodegenerative diseases are dementia, Parkinson's disease, Alzheimer's disease, vascular dementia, dementia with Lewy bodies, Huntington's disease, progressive supranuclear palsy, frontotemporal dementia, Creutzfeldt-Jakob disease, Wernicke-Korsakoff syndrome.

Embodiment 37. The method according to embodiment 31, wherein the sleep deprivation and/or insufficient sleep are due to a sleep disorder.

Embodiment 38. The method according to embodiment 37, wherein sleep the disorder is sleep apnea, narcolepsy, insomnia and/or parasomnia.

Embodiment 39. The method according to any one of embodiments 30-38, wherein the cognitive impairments are due to mental fatigue.

Embodiment 40. The method according to embodiment 39, wherein mental fatigue includes symptoms of attention deficiencies, lack of focusing, forgetfulness, lack of productivity, lack of concentration, reduced mental clarity, problem paying attention, short attention span and learning difficulties.

Embodiment 41. The method according to any one of the embodiments 30-40, wherein the bacterial strain of the species *Lacticaseibacillus paracasei* or a mixture thereof is a probiotic strain.

Embodiment 42. The method according to any one of the embodiments 30-41, wherein the strain of the species *Lacticaseibacillus paracasei* is strain Lpc-37, registered at the DSMZ under deposit number DSM32661 on 5 Oct. 2017.

Embodiment 43. The method according to any one of embodiments 30-41, wherein said composition comprises further bacteria.

Embodiment 44. The method according to embodiment 43, wherein said further bacteria is strain Lp-115 and/or strain B420, registered at the DSMZ under deposit number DSM32073 on 30 Jun. 2015.

Examples

The following examples are provided to demonstrate and further illustrate specific embodiments and aspects of the present invention and are not to be construed as limiting the scope thereof.

Study Rationale

Insufficient sleep is a serious public health epidemic in modern society, leading to impairment of memory and other cognitive functions. Probiotics could offer a novel approach to improve cognitive performance through the microbiota-gut-brain axis. In this study, partial sleep deprivation was used to induce cognitive impairment in mice and to determine the effects of probiotics. *Lacticaseibacillus paracasei* Lpc-37 (Lpc-37), *Lactiplantibacillus plantarum* Lp-115 (Lp-115), *Bifidobacterium animalis* ssp. *lactis* 420 (B420) and their combination were tested in mice subjected to partial sleep deprivation and compared with non-sleep deprived and sleep deprived vehicle groups (placebo groups). Mice were administered a daily oral gavage containing either 1×10⁹ colony forming units (CFU) of bacterial single-strain, 1.5×10⁹ CFU of bacterial multi-strain, or vehicle for thirty days prior to and for nine days during a behavioural test paradigm. Behavioural tests, including novel object recognition (NOR), spontaneous alternation Y-maze (Y-maze) and step-through passive avoidance (STPA) task, were applied to evaluate learning and memory performances following partial sleep deprivation.

Study Design

Overall Study Design and Plan

Animals

Five-week-old male Swiss mice weighing 30-35 g were purchased from JANVIER (Saint Berthevin, France). Mice were group housed in a temperature and humidity-controlled animal facility with a 12 h light/dark cycle (lights off at 7 pm). Mice were housed six per cage with access to food (SAFE A04C, SAFE, Route de Saint Bris, 89290 AUGY, France) and water ad libitum and all mice in a cage receiving the same treatment. The study was conducted at Amylgen's animal facility (Approval #A-34-169-002) in accordance with the recommendations of the Directive 2010/63/UE of the European Parliament and of the Council of 22 Sep. 2010. The protocol was approved by the Languedoc Roussillon Ethic Committee CE2A-36. Routinely, the overall health (hair and eyes) and activity/condition (locomotor activity and posture) of the mice were visually monitored daily. Weight measurements were recorded three times per week.

Experimental Design and Probiotic Intervention

Mice were randomly assigned to six treatment groups (n=12 per group): Non-sleep deprived vehicle (no SD/Veh), sleep deprived vehicle (SD/Veh), and four sleep deprived groups supplemented with a single strain Lp-115 (SD/Lp-115), Lpc-37 (SD/Lpc-37), B420 (SD/B420) or bacterial multi-strain (Lpc-37+Lp-115+B420; SD/multi-strain).

Figure 4:
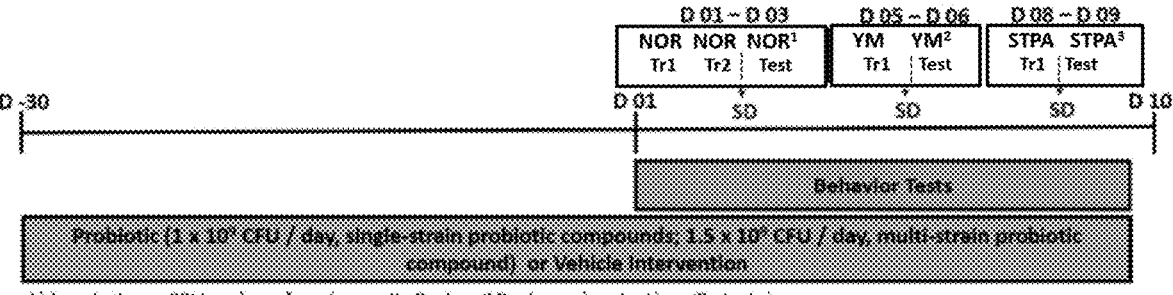
FIG. 4. Scheduling of the procedure in the experimental design and probiotic intervention. Three individual probiotic strains and their three-strain combination were tested in mice subjected to sleep deprivation (SD) and compared with non-sleep-deprived (No SD/Veh) and sleep-deprived vehicle (SD/Veh) groups. Mice were administered a daily oral gavage containing either $1 \times 10^9$ colony forming units of bacterial single-strain, $1.5 \times 10^9$ colony forming units of bacterial combination or vehicle for thirty days prior to and for nine days during a behavioural test paradigm. Behavioural tests were applied to evaluate learning and memory performances following a 5 h SD period. The behavioural tests used included the novel object recognition test (NOR; days one to three), the Y-maze spontaneous alternation test (Y-maze; days five and six) and the step-through passive avoidance task (STPA; days eight and nine), with two days of rest on days four and seven.

The experimenter involved in the treatment and care of the mice was blind to the experimental treatment groups and a number was assigned to each treatment to maintain the blinded condition. Mice in the probiotic treatment groups were perorally gavaged with either 1×10⁹ colony forming units (CFU) of single bacterial strain or 1.5×10⁹ CFU of bacterial multi-strain (Lp-115 at 5×10⁸ CFU, Lpc-37 at 5×10⁸ CFU, and B420 at 5×10⁸ CFU). Freeze-dried bacterial cultures were produced by Danisco Cultures, a division of Danisco USA Inc. (DuPont Nutrition Biosciences; Madison, WI) and freshly diluted into 100 μl of saline (0.9% NaCl in double-de-ionized water) each day to achieve the correct doses. Vehicle mice were perorally gavaged with 100 μl per day of saline solution only. Bacterial intervention continued daily for thirty days prior to, and for nine days during a behavioural test paradigm, until the last day of behavioural assessments. On day ten, the day after the last behaviour test, all mice (n=72) were anesthetized with 4% isoflurane and sacrificed by cervical dislocation. The scheduling of procedures is shown schematically in FIG. 4.

Behavioural Test Paradigm

Following thirty days of probiotic or vehicle intervention, all mice underwent a behavioural test paradigm to measure cognitive function (learning and memory) following sleep deprivation. The novel object recognition (NOR) test was used to measure short-term nonspatial recognition memory; the Y-maze spontaneous alternation (Y-maze) test was used to measure spatial working memory of short-term work, and the step-through passive avoidance (STPA) task was used to measure contextual long-term memory.

Behavioural assessments were performed over nine consecutive days:

day 1) NOR (habituation);
day 2) NOR (same object session);
day 3) NOR (novel object session);
day 4) rest;
day 5) Y-maze (training session);
day 6) Y-maze (test session);
day 7) rest;
day 8) STPA (training session) and
day 9) STPA (testing session).

On day two, day five and day eight, immediately after the training sessions of each behavioural test, mice were submitted to sleep deprivation for 5 h before the start of the activity phase (7 pm).

All behavioural tests were performed in specially equipped rooms within the animal facility. To minimize stress, mice were habituated to the testing room by placing home-cages there for at least 30 min prior to testing. The same mice were assessed across all behavioural tests. A researcher who was blinded to the group designations remained in the testing room during each behavioural test. In addition, all outputs were measured by an experimenter blinded to the experimental groups.

Sleep Deprivation Procedure

Partial sleep deprivation was induced using the "gentle handling" method by a fully trained technician who was familiar with the mice prior to the procedure. The "gentle handling" method consisted of keeping mice randomly allocated to sleep deprivation groups awake by gentle manipulations whenever behavioural signs of sleep (i.e. drowsiness or attempts to engage in a sleeping posture) were observed. Mice were sleep deprived for 5 h in their home cage, before the onset of the activity phase (7 pm), immediately after the training sessions of each behavioural test on days two, five and eight.

Endpoint Measurements

Novel Object Recognition (NOR) Test

The NOR test exploits the natural tendency of mice to explore novel objects and measures the amount of time spent with a novel versus a familiar object. The test consisted of a habituation phase (day one), a training phase (day two) and a testing phase (day three).

Prior to assessment of NOR, all mice were habituated to the testing arena to measure anxiety-related behaviour, locomotor activity and stereotypic behaviours (e.g. rearing and grooming). The open field (OF) arena is a white plexiglass open arena (50 cm×50 cm×55 cm) with a floor equipped with diodes emitting infrared light. Mice were placed in the centre of the softly illuminated (100 lux) OF arena and allowed 10 min free exploration in the arena during which time their locomotor activity and behaviour was recorded using an infrared-sensitive camera connected to a computer. Time spent and locomotor activity in the centre of the arena, total locomotor activity and stereotypies were analysed with Ethovision® XT12 software (Noldus).

On day two, 24 h following the OF test, mice were reintroduced to the same arena containing two identical objects placed in opposite corners of the arena, approximately 5 cm from each wall. Mice were allowed 10 min free exploration time in the arena and during this time behaviour was recorded using an infrared-sensitive camera connected to a computer.

On day three, 24 h after the training phase, mice were reintroduced to the arena, this time containing one familiar object and one novel object (the object in position two from day 2 was replaced with a novel object which differed from the familiar one in colour, shape and texture). Mice were allowed to freely explore the arena for 10 min, during such time behaviour was recorded using an infrared-sensitive camera connected to a computer. The apparatus and objects between mice were cleaned using 50% vol/vol ethanol. After each day, mice were returned to their home cages with cagemates.

Cognitive function was analysed by measuring the preference index (PI) and the discrimination index (DI). Object exploration was defined as the time when the mouse's nose came within a 2 cm radius of the object and when the direction of the head was pointed to the object. The PI was calculated as the frequency or duration of contacts with the object in position two over the total frequency or duration of contacts with both objects (in position one and position two). The DI for the novel object was calculated as the difference of time mice spent investigating between the novel and the familiar object divided by the total time exploring both objects. [Discrimination Index, DI=(Novel Object Exploration time−Familiar Object Exploration time)/(Novel Object Exploration time+Familiar Object Exploration time)]. In the DI, the result can vary between +1 (i.e. more time spent with the novel object) and −1 (i.e. more time spent with the familiar object), with 0 indicating equal time spent between the novel and familiar object. Mice showing less than ten contacts with objects on day two and day three were discarded from the assessment.

Spontaneous Alternation Y-Maze Test

The Y-maze test is based on the innate tendency of mice to alternate between exploring different arms of a maze. The test consisted of a training phase (day five) and a testing phase (day six).

The Y-maze was made from grey polyvinylchloride and each arm was 40 cm long, 12 cm high, 3 cm wide at the bottom and 10 cm wide at the top and converged in an equilateral triangular central area. On day five and day six, mice were individually placed at the end of one arm of the maze and allowed to move freely through the maze during an 8 min session. The series of arm entries was recorded visually by a trained technician. The apparatus and objects between mice were cleaned using 50% vol/vol water/ethanol. After each day, mice were returned to their home cages with cagemates. On day five, immediately after the training phase, mice were submitted to sleep deprivation for 5 h before the start of the activity phase (7 pm).

An alternation was defined as consecutive full entries (excluding the tail) into each of the three arms. The number of maximum alternations was calculated as the total number of arm entries minus two, and the percentage of alternation was defined by the following formula: [(alternations)/(total entered−2)×100]. Mice showing more than 10 arm entries, or an alternation percentage less than 20% or greater than 90% on both days were discarded from the assessment.

Step-Through Passive Avoidance (STPA) Task

The STPA task is an index of contextual long-term memory used to assess memory formation. The task consisted of a training phase (day eight) and a testing phase (day nine).

The apparatus consisted of a two-compartment box (15 cm×20 cm×15 cm) with a bright enclosure illuminated with white polyvinylchloride walls and a dark enclosure with black polyvinylchloride walls, connected by a retractable door. On day eight, each mouse was placed in the bright compartment. After 5 seconds, the retractable door was lifted. When the mouse entered the dark compartment, the door was closed and a scrambled foot shock (0.3 mA, 3 seconds duration) was delivered through a grid floor using a shock generator scrambler (Lafayette Instruments, Lafayette, USA). The time from the light compartment to the electric grid floor for each individual mouse was considered a measure of step through latency time, and the step-through latency to enter was recorded. On day eight, immediately after the training phase, mice were submitted to sleep deprivation for 5 h before the start of the activity phase (7 pm).

On day nine, 24 h after training, the mouse was returned to the bright compartment and the measure of learning was the time taken to again enter the dark compartment. After 5 seconds, the door was elevated. A step-through latency up to a 300 seconds cut-off time was established if the animal did not cross the dark enclosure. The step-through latency to escape to the bright compartment was also recorded. The apparatus and objects between mice were cleaned using 50% vol/vol water/ethanol. After each day, mice were returned to their home cages with cagemates.

Statistical Analyses

All values, except passive avoidance latencies, are expressed as mean±standard error of the mean (SEM). All data were first checked for normality using the Shapiro-Wilk test, and then analysed using one-way ANOVA followed by Dunnett's multiple comparisons test or two-way ANOVA followed by Sidak's multiple comparisons test, if the data were normally distributed. Non-normally distributed data (i.e. passive avoidance latencies) were analysed using the non-parametric Kruskal-Wallis test, followed by Dunn's test for multiple comparisons. All data were analysed using GraphPad Prism software v.6 (GraphPad Software Inc., La Jolla, CA, USA). A p-value lower than 0.05 was considered statistically significant.

Results and Comments

Novel Object Recognition (NOR) Test (Recognition Memory; FIG. 1)

The NOR test was used to assess the effect of probiotics on the short-term nonspatial recognition memory ability of sleep-deprived mice; the results are shown in FIG. 1.

During the second day of the NOR test and prior to sleep deprivation, there was no significant effect of the bacterial interventions on the interaction frequency (FIG. 1A) or on object interaction time (FIG. 1B) of the two similar objects, compared to the vehicle groups.

Sleep deprivation immediately following the acquisition of the memory, i.e. familiar objects (day two of the NOR test) induced a significant disruption in the ability to recognize the familiar object on day three of the NOR test. While the no SD/Veh group had a significantly higher interaction frequency (p<0.05; FIG. 1C) and interaction time (p<0.001; FIG. 1D) with the novel object, compared to the theoretical value of 50%, this same result was not observed in the SD/Veh group. Following intervention with Lpc-37, and despite the period of sleep deprivation, mice in the SD/Lpc- 37 group had a significantly higher interaction frequency (p<0.05; FIG. 1C) and interaction time (p<0.001; FIG. 1D) with the novel object, compared to the theoretical value of 50%. Similarly, SD/multi-strain-treated mice showed an increase in the interaction frequency (p<0.01; FIG. 1C) and interaction time (p<0.001; FIG. 1D) with the novel object, compared to the theoretical value of 50%. Similar to the SD/Veh group, intervention with Lp-115 or B420 did not prevent the recognition memory deficits caused by sleep deprivation (FIGS. 1C and 1D).

It appeared that sleep deprivation had no effect on the DI for object interaction frequency of contact since the SD/Veh group was not significantly different to the no SD/Veh group (FIG. 1E). Furthermore, there was no effect of bacterial intervention on this DI measure when comparing the treatment groups with the SD/Veh (FIG. 1E). In the DI for time of interaction, a statistical difference was observed in the SD/Veh group compared to the no SD/Veh group (p<0.001; FIG. 1F). Lpc-37 (p<0.001) and the multi-strain (p<0.001) had a significantly greater ability to discriminate between the novel and familiar objects, even after partial sleep deprivation, reflected in the DI for time of interaction, compared to the SD/Veh group (FIG. 1F). Similar to the SD/Veh group, intervention with Lp-115 or B420 did not result in a greater ability to discriminate between the novel and familiar objects in this index (FIG. 1F). Lpc-37 and the multi-strain did not significantly differ from the no SD/Veh group (FIG. 1F).

Statistical Analysis: All data were analysed using the one-way ANOVA (F value) and Dunnett's test for multiple comparisons. The statistical analyses for object interaction frequency (%) and object interaction time (%) were compared to a theoretical value of 50% (or "0" for the DI). Unless otherwise stated, n=12 for all groups. Data is expressed as mean±SEM.

$ p<0.05, $$ p<0.01 vs. theoretical value of 50% (C); $$$ p<0.001 vs. theoretical value of 50% (D); *** p<0.001 vs. No SD/Veh group (F); ###p<0.001 vs. SD/Veh group (1F).

Figure 2:
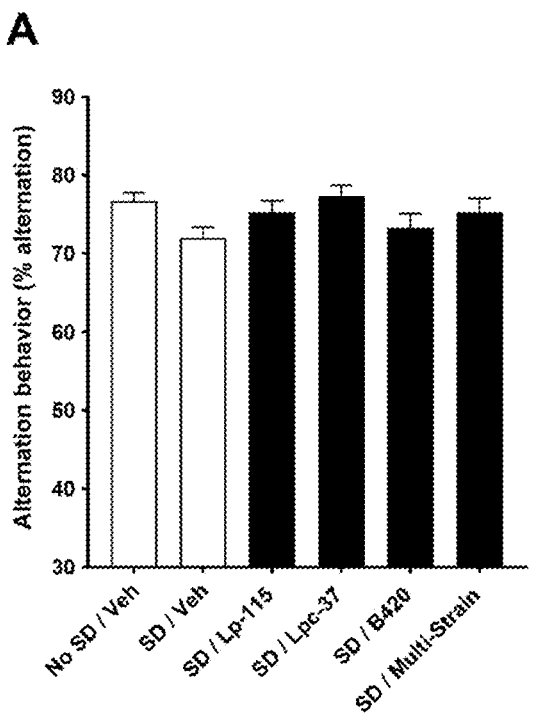
FIG. 2. Y-maze spontaneous alternation test (spatial working memory). Effects of probiotic intervention on spatial working memory deficits induced by sleep deprivation (SD). Cognitive function in the Y-maze spontaneous alternation test following administration of either $1 \times 10^9$ colony forming units of bacterial strain (Lp-115 or Lpc-37 or B420), $1.5 \times 10^9$ colony forming units of bacterial combination (Lp-115+Lpc-37+B420) or vehicle for 30 days prior to and for 9 days during a behavioural test paradigm. (A and B) Alternation behaviour (%) and locomotion (arm entries) on training day (Day 5), respectively. (C and D) Alternation behaviour (%) and locomotion (arm entries) on test day (Day 6), respectively.
Figure 2:
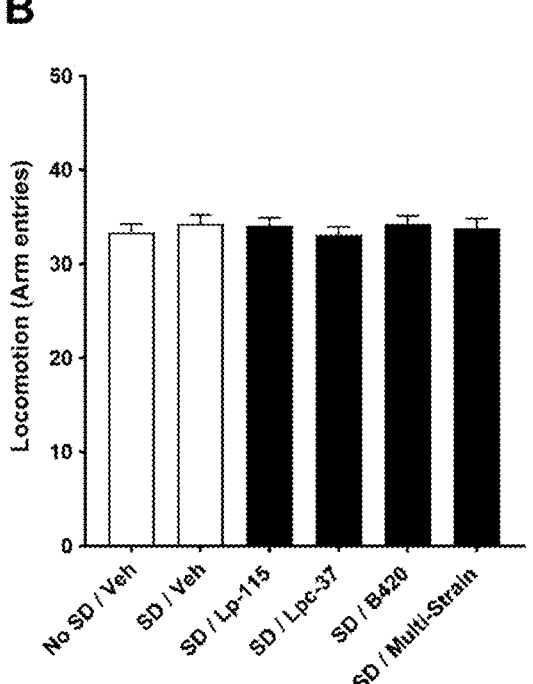
Figure 2:
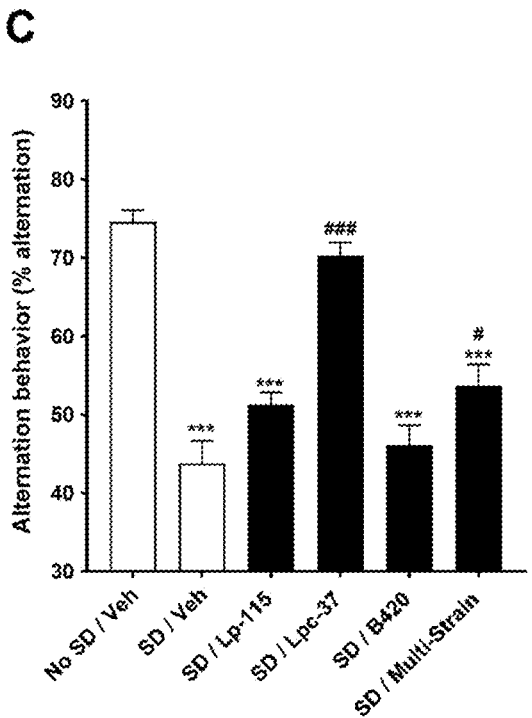
Figure 2:
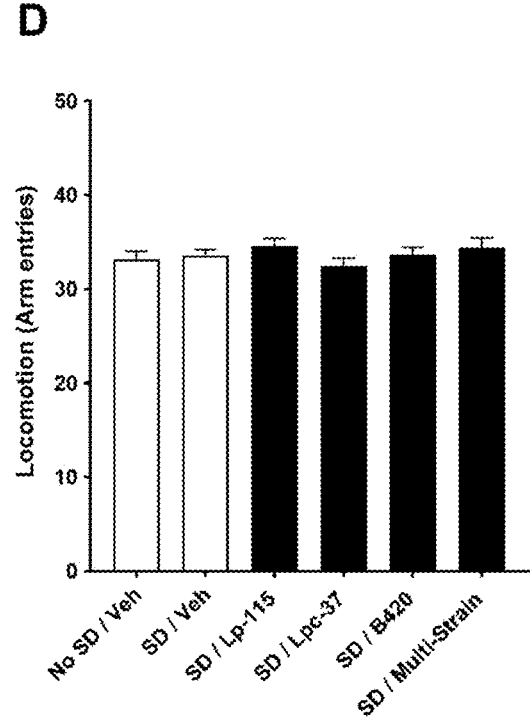

Y-Maze Spontaneous Alternation Test (Spatial Working Memory; FIG. 2)

The Y-maze spontaneous alternation test was used to assess the effect of probiotics on spatial working memory in sleep-deprived mice, and the results are shown in FIG. 2.

On day five, during the training session of the spontaneous alternation Y-maze test and prior to sleep deprivation, none of the treatment groups were significantly different to the vehicle groups for spontaneous alternation behaviour (FIG. 2A). Furthermore, there was no effect of the bacterial interventions on locomotion or arm entries, compared to the vehicle groups (FIG. 2B). Sleep deprivation immediately following the acquisition of the memory, i.e. assessment of spatial learning and reference memory induced a significant disruption to spatial working memory in the Y-maze test on day six of the behavioural test paradigm. During the testing session, mice in the SD/Veh group exhibited a significant reduction in spontaneous alternation, compared to the no SD/Veh group (p<0.001; FIG. 2C). Sleep deprivation had no effect on locomotion or arm entries and there was no significant difference between the vehicle groups (FIG. 2D). Following intervention with Lpc-37, and despite the period of sleep deprivation, mice in the SD/Lpc-37 group had a significant increase in spontaneous alternation behaviour, compared to the SD/Veh group (p<0.001; FIG. 2C). Furthermore, Lpc-37 did not significantly differ from the no SD/Veh group (p>0.05; FIG. 2C). A partial restoration of spontaneous alternation behaviour was observed after intervention with the bacterial multi-strain, compared to the SD/Veh group (p<0.05; FIG. 2C). Similar to the SD/Veh group, intervention with Lp-115 or B420 did not increase spontaneous alternation behaviour (FIG. 2C). There was no significant effect of the treatments on locomotion or arm entries, compared to the vehicle groups (FIG. 2D).

Statistical Analysis: All data were analysed using the one-way ANOVA (F value) and Dunnett's test for multiple comparisons. Unless otherwise stated, n=12 for all groups. Data is expressed as mean±SEM.

*** p<0.001 vs. No SD/Veh group (C); #p<0.05, ###p<0.001 vs. SD/Veh group (2C).

Figure 3:
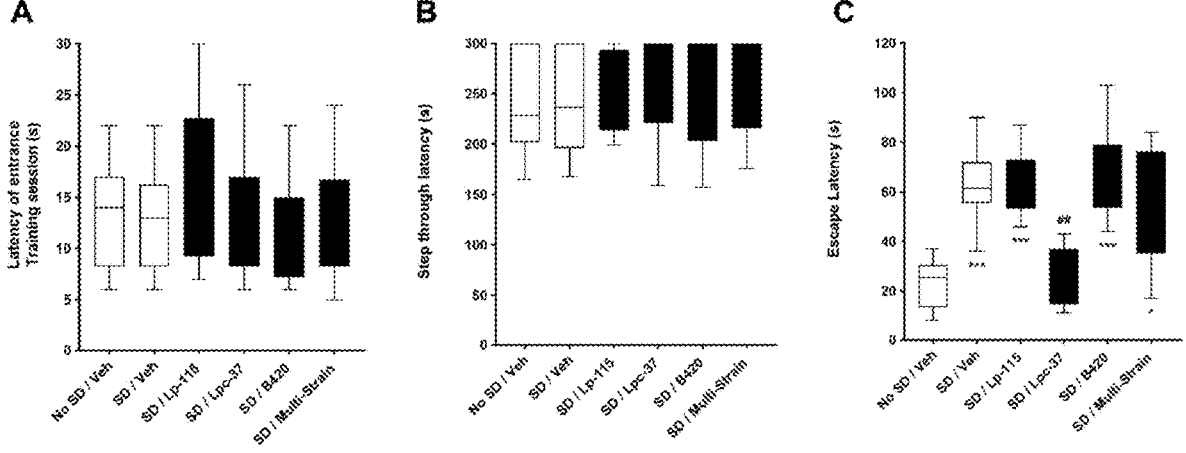
FIG. 3. Step-through passive avoidance task (contextual long-term memory). Effects of probiotic intervention on contextual long-term memory induced by sleep deprivation (SD). Cognitive function in the step-through passive avoidance task following administration of either $1 \times 10^9$ colony forming units of bacterial strain (Lp-115 or Lpc-37 or B420), $1.5 \times 10^9$ colony forming units of bacterial combination (Lp-115+Lpc-37+B420) or vehicle for 30 days prior to and for 9 days during a behavioural test paradigm. (A) Latency of entrance (s) on training day (Day 8). (B) Step-through latency (s) on test day (Day 9). (C) Escape latency (s) on test day (Day 9).

Step-Through Passive Avoidance (STPA) Task (Contextual Long-Term Memory; FIG. 3)

The STPA task was used to assess the effect of probiotics on contextual long-term memory in sleep-deprived mice, and the results are shown in FIG. 3.

On day eight, during the training session of the STPA task and prior to sleep deprivation, mice across all treatment groups exhibited no significant differences in step-through latency time, compared to the vehicle groups (FIG. 3A). Sleep deprivation immediately following the acquisition of the memory, i.e. association of a foot shock within the dark compartment, induced a significant disruption to contextual long-term memory in the STPA task on day nine of the behavioural test paradigm. During the testing session, step through latency time was similar in the no SD/Veh group, compared to the SD/Veh group (FIG. 3B), and there were no significant effects of the bacterial interventions on the step through latency time, compared to the SD/Veh group (FIG. 3B). All mice, whether sleep-deprived or not, resisted entry to the dark chamber and used the maximum allowed time of 300 seconds before being manually moved into the dark compartment. Once inside the dark compartment, the SD/Veh group had a significantly increased escape latency, or were significantly slower to exit the dark compartment, compared to the no SD/Veh group (p<0.001; FIG. 3C). Mice in the SD/Lpc-37 group were the only treatment group that had a significant reduction in escape latency time, compared to the SD/Veh group (p<0.001; FIG. 3C). Furthermore, the SD/Lpc-37 group was the only treatment group that was not significantly different to the no SD/Veh group for escape latency time, indicating that intervention with Lpc-37 seemingly normalized the effects of sleep deprivation to that of the no SD/Veh group.

Statistical Analysis: All data were analysed using the Kruskal-Wallis non-parametric ANOVA (H value) and Dunn's test for multiple comparisons. Unless otherwise stated, n=12 for all groups. Data is expressed as mean±SEM.

* p<0.05, *** p<0.001 vs. No SD/Veh group; ##p<0.01 vs. SD/Veh group (C).

General Conclusions from the Results

The following conclusions can be drawn from the results described above.

Partial sleep deprivation had a significant impact on cognitive function in sleep-deprived vehicle mice (No SD/Veh and SD/Veh);

Intervention with Lpc-37 significantly improved sleep deprivation-induced recognition memory deficits in NOR, spatial working memory deficits in Y-maze, and contextual long-term memory impairments in STPA;

The bacterial multi-strain (Lp-115+Lpc-37+B420) significantly improved sleep deprivation-induced recognition memory deficits in NOR and spatial working memory deficits in Y-maze;

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method for treating cognitive impairments induced by sleep deprivation or insufficient sleep or both in a subject in need thereof, wherein the sleep deprivation or the insufficient sleep or both are due to a sleep disorder, comprising:

administering to the subject an effective amount of a combination of DGCC4981 (Lpc-37), registered at the DSMZ under deposit number DSM3261 on Oct. 5, 2017 of the species *Lacticaseibacillus paracasei, Lactiplantibacilllus plantarum* strain Lp-115, and *Bifidobacterium animalis* ssp. *lactis* DGCC420 (B420) registered at the DSMZ under deposit number DSM32073 on Jun. 30, 2015.

2. The method according to claim 1, wherein the sleep disorder is selected from one or more of sleep apnea, narcolepsy, insomnia and parasomnia.

3. The method according to claim 1, wherein the combination is administered to the subject as part of a food product, a food ingredient, a dietary supplement or a pharmaceutical composition.

4. The method according to claim 1, wherein the effective amount is $1.5 \times 10^9$ Colony-Forming Units of the combination per dose.

5. The method according to claim 1, wherein the effective amount ranges from $10^6$ Colony-Forming Units to $10^{12}$ Colony-Forming Units of the combination per dose.

* * * * *